(12) United States Patent
Smith et al.

(10) Patent No.: US 6,964,782 B1
(45) Date of Patent: Nov. 15, 2005

(54) STABLE HYDROGEN PEROXIDE COMPOSITIONS, PRODUCTS AND METHODS OF USE

(75) Inventors: Robert Lee Smith, Albany, OR (US); Steven Dale Smith, Jefferson, OR (US); Wendy S. Langley, Albany, OR (US); John Mark Christensen, Corvallis, OR (US); Vernon W. Smith, Albany, OR (US)

(73) Assignee: Tec Labs, Inc., Albany, OR (US)

( * ) Notice: Subject to any disclaimer, the term of this patent is extended or adjusted under 35 U.S.C. 154(b) by 78 days.

(21) Appl. No.: 10/616,047

(22) Filed: Jul. 7, 2003

Related U.S. Application Data

(60) Provisional application No. 60/397,997, filed on Jul. 23, 2002.

(51) Int. Cl.[7] .................. A61K 9/12; A61K 33/40; A01N 25/16; A01N 59/00; A61L 17/02

(52) U.S. Cl. ............... 424/616; 424/78.02; 424/78.05; 424/78.06; 424/78.07; 424/407; 424/600; 424/603; 424/641; 424/642; 424/690; 424/724; 424/760; 424/770; 424/777; 514/159; 514/161; 514/162; 514/163; 514/164; 514/171; 514/179; 514/238.8; 514/309; 514/312; 514/317; 514/352; 514/356; 514/535; 514/536; 514/537; 514/620; 514/670; 514/692; 514/728; 514/730; 514/731; 514/734; 514/762; 514/778; 514/785; 514/789; 514/945; 514/970

(58) Field of Search .................. 424/45, 49, 52–56, 424/58, 400, 616, 78.02, 78.05, 78.06, 78.07, 424/407, 600, 603, 641, 642, 690, 724, 760, 424/770, 777; 514/945, 887, 159, 161–164, 514/171, 238.8, 309, 312, 317, 352, 356, 514/535–537, 620, 670, 692, 728, 730–731, 514/734, 762, 778, 785, 789, 970

(56) References Cited

U.S. PATENT DOCUMENTS

| | | | |
|---|---|---|---|
| 4,781,923 A | 11/1988 | Pellico | 424/130 |
| 5,174,990 A | 12/1992 | Douglas | 424/53 |
| 5,336,432 A | 8/1994 | Petchul et al. | 252/186.43 |
| 6,086,856 A | 7/2000 | Saferstein | 424/58 |
| 2002/0114847 A1 | 8/2002 | Peshoff | |
| 2002/0136756 A1 | 9/2002 | McAdams | |

*Primary Examiner*—John Pak
(74) *Attorney, Agent, or Firm*—Lori M. Friedman

(57) ABSTRACT

Disclosed are several preferred embodiments of hydrogen peroxide which are packaged with ease of use and extended shelf-life in mind. The embodiments include foam, mist, gel, and disposable towelette forms of $H_2O_2$. Optional ingredients of topical pain relievers and skin protectants are also disclosed, as are their methods of use.

10 Claims, No Drawings

STABLE HYDROGEN PEROXIDE COMPOSITIONS, PRODUCTS AND METHODS OF USE

RELATED PATENT APPLICATIONS

This is a utility patent application based on U.S. provisional patent application Ser. No. 60/397,997 filed Jul. 23, 2002.

BACKGROUND OF THE INVENTION

1. Field of the Invention

The present invention relates to stable hydrogen peroxide antiseptic compositions that allow facile application of the peroxide to skin in response to a cut or other minor injury that would benefit from antiseptic application. More specifically, the invention addresses the benefits afforded by the application of $H_2O_2$ in the form of a stable, easily administered foam, mist, gel, or disposable towelette.

2. Background of Related Art

Currently hydrogen peroxide is made and sold as an aqueous 3% solution that is applied as an antiseptic to the affected area of the skin. It is a low viscosity, runny substance that is usually applied with absorbent cotton. This procedure can be messy and inconvenient. Having a stable, non-runny hydrogen peroxide solution that can be used without the need for additional application means, such as cotton balls, gauze, cotton swabs, or tissues would serve the needs of many users of this common antiseptic.

Aqueous solutions containing hydrogen peroxide at a concentration level from about 1 to about 10% have long been known for their antiseptic properties. While it is reported in the literature that the antiseptic characteristics of hydrogen peroxide arise by virtue of the oxidizing properties of this composition, it has also been suggested that the mode of action of hydrogen peroxide is through the production of a strong oxidant, namely, the hydroxyl free radical.

In any case, there is continual interest in the utilization of hydrogen peroxide solutions as antiseptic compositions. These solutions are generally available as aqueous compositions containing 3.0 weight percent hydrogen peroxide. As has been stated, these aqueous compositions have certain disadvantages. One notable disadvantage is that in applying the liquid peroxide composition to skin cuts or abrasions, the amount utilized treating the wound compared to the amount applied to the wound is minimal since most of the liquid immediately flows away from the application site. Another problem encountered with the liquid is that it is difficult to apply to certain areas of the body and must be cautiously applied to other areas of the body such as, for example, in the vicinity of the eyes. Also, since hydrogen peroxide solutions may degrade faster when agitated, their utilization as a portable antiseptic for camping, hiking and other outdoor activities is limited. Application of liquid $H_2O_2$ to a topical wound may be accompanied by accidental application of contaminants to a wound by the use on non-sterile application means. Contamination can also result when and if foreign objects are introduced t the hydrogen peroxide bottle.

Another negative factor concerning liquid $H_2O_2$ is the fact that the material is inherently unstable. Packaged in opaque bottles, aqueous $H_2O_2$ is not a stable solution. The reaction that yields water and oxygen from the degradation of hydrogen peroxide is $$2H_2O_2 \rightarrow 2H_2O + O_2.$$

The energy levels of the stable water and oxygen reaction products are much lower than is the energy of the unstable hydrogen peroxide molecule. Light catalyzes the reaction, thus packaging for typical, prior art hydrogen peroxide liquid products are opaque.

In U.S. Pat. No. 4,781,923 Pellico formulated an antiseptic gel which comprises polyglyceryl methacrylate hydrate gel and hydrogen peroxide. In the gel compositions of '923, there is much more polyglyceryl methacrylate hydrate in the gel than there is hydrogen peroxide. The instant invention comprises only $H_2O_2$ as the active antiseptic ingredient. Pellico has admixed $H_2O_2$ with a gelled methacrylate.

Additional prior art on hydrogen peroxide (in concentrations less than 10%) include numerous patents and patent applications on hydrogen peroxide in non-bleaching dental uses such as U.S. Pat. No. 6,086,856 to Saferstein et al.

This patent combines $H_2O_2$ with a variety of ingredients with specific dental uses such as antimicrobial agents, anti-plaque agents and anti-cariogenic agents. Such compositions are not like the $H_2O_2$ compositions of the present invention.

Another prior patent, U.S. Pat. No. 5,174,990 to Douglas relates to a mouth rinse. Again the non-peroxide ingredients are numerous and the $H_2O_2$ of the formulation is present in less than 1%. Ingredients of the Douglas invention include those which are different in kind to those of the present invention including zinc chloride, sodium citrate, sodium lauryl sulfate, citric acid, and ethanol.

When looking for $H_2O_2$ patented for topical wound healing purposes as is the instant invention, both published U.S. patent applications and issued U.S. patents were found. In the category of published patent applications is U.S. 2002/0114847 to Peshoff. Disclosed therein are anti-fungal, antiseptic compositions including those containing zinc oxide and fat-soluble vitamins, which are not akin to the instant compositions.

U.S. patent application U.S. 2002/0136756 A1 to McAdams discloses a sub-epidermal which abrades the skin. The invention as described is totally unlike the present invention.

U.S. Pat. No. 5,336,432 to Petchul et al concerns a water and oil emulsion of hydrogen peroxide and various other ingredients having bleaching and antiseptic properties. Applicants' invention is one phase with no oil ingredients whatsoever.

Applicants have discovered a way to make $H_2O_2$ into a stable foam, mist or gel product. This is a noteworthy improvement not only for ease by an end user but especially in light of the scientific and packaging difficulties in achieving stable foam, mist, or gel product out of the basically unstable $H_2O_2$ molecule.

The hydrogen peroxide of this invention consists of hydrogen peroxide, in concentration up to 15 weight percent, a surfactant, and a stabilizer. A variety of optional ingredients, tailored for the use of the end user, may be included. Such ingredients include topical pain relievers and skin protectants. The $H_2O_2$ antiseptic is stable and is made in a variety of stable, user-friendly forms.

Accordingly, it would be advantageous to provide a stable and adherent hydrogen peroxide composition which overcomes the disadvantages that are present in currently available hydrogen peroxide products.

SUMMARY OF THE INVENTION

In accordance with one aspect of this invention, there is provided a stable, easily dispensed foam of $H_2O_2$ that is dispensed from a finger depressing foam dispenser. The foam so dispensed keeps hydrogen peroxide on the affected area. Having it vanish after rubbing into the skin makes the product less messy and control by the user is greater than the current liquid $H_2O_2$ product.

In accordance with another aspect of this invention, a sprayable foam of $H_2O_2$ is provided. This foam is convenient an easy for a consumer to use in the home or when outdoors where the usual application means may not be readily available. When used in the home, the disadvantages of $H_2O_2$ applied with absorbent cotton, such as accidental contamination of the peroxide solution, may occur.

In accordance with a third aspect of this invention, a disposable towelette may be saturated with $H_2O_2$ and factory-sealed in a foil packet for ease of use by a consumer. Not only is this packaging convenient for use when traveling or in the outdoors, but any worries of accidental contamination by the application means are negated.

In accordance with a fourth aspect of this invention, a stable gel of hydrogen peroxide is provided. The convenience and advantages of this form of $H_2O_2$ include reduced degradation into water and oxygen, reduced flow of active ingredient away from the injury, and ease of application.

This invention provides stable and adherent hydrogen peroxide formulations which overcome many of the disadvantages that are inherent in the aqueous hydrogen peroxide antiseptic solutions of the prior art. Also disclosed are methods for synthesis, packaging and use of several different and unique forms of antiseptic hydrogen peroxide.

DETAILED DESCRIPTION OF PREFERRED EMBODIMENTS

The hydrogen peroxide compositions of this invention are compounded to facilitate convenient and safe application of the antiseptic to minor topical wounds often encountered. More particularly, the antiseptic hydrogen peroxide is formulated as a foam, spray, gel or towelette which are applied to the wound without the need for additional application means, such as absorbent cotton. The formulations also may contain additional ingredients, such as topical pain relievers and skin protectants, which are complementary to the antiseptic properties of $H_2O_2$.

A first embodiment of the uniquely compounded $H_2O_2$ of this invention is in the form of a foam. The significance of a topical treatment dispensed as a foam include that it will not run and it holds the active ingredient on the skin where it is needed. Another advantage of $H_2O_2$ in the form of a foam is that additional application means, such as absorbent cotton, are not needed. This advantage is due to convenience as well as safety, since misapplication can lead to infection or additional injury.

The $H_2O_2$ foam of this invention is an aqueous solution of hydrogen peroxide comprises a 0.1% to 15% solution of $H_2O_2$, about 1% of a surfactant, and less than 1% of a stabilizer. In this invention, all percentages given for formulations are weight percents. The foam that is produced is packaged in a container equipped with a pump foaming chamber that produces. foam without the use of gas propellants and delivers $H_2O_2$ topically to a wound by finger-depression of a foam dispenser.

A typical laboratory procedure that yields a typical foam of $H_2O_2$ is as follows. To make 100 grams of the stable hydrogen peroxide foam of this invention, 97.2 grams of purified water are placed in a beaker. Added to the water is a surfactant, such as octylnol 9, laneth-4, steareth-4, oleth-4, ceteth-10, laneth-10, steareth-10, oleth-10, ceteth-20, polysorbates 20 and 80, and combinations thereof. These surfactants/non-ionic detergents that are commonly used in pharmaceutical, biochemical and chemical syntheses, and are octylphenol ethylene oxide condensates.

The solution is mixed until the surfactant is thoroughly dispersed. To this solution is then added 0.05 gram of a stabilizer, sodium pyrophosphate, which is mixed until dissolved. While stirring slowly, 8.68 grams of 35% $H_2O_2$ is added until it is thoroughly dispersed. The mixture of $H_2O_2$, surfactant, and stabilizer is added to a pump foaming chamber.

Optional ingredients that may be present in the hydrogen peroxide foam embodiment of this invention include topical pain relievers and skin protectants. The topical pain relievers are used to kill pain which may accompany the wound being treated. They may be selected from the group consisting of benzocaine, butamben picrate, dibucaine hydrochloride, dimethisoquin hydrochloride, dyclonine hydrochloride, lidocaine, lidocaine hydrochloride, pramoxine hydrochloride, tetracaine, tetracaine hydrochloride, benzyl alcohol, camphor, camphorated metacresol, juniper, menthol, phenol, phenolate sodium, resorcinol, diphenhydramine hydrochloride, tripelenamine hydrochloride, hydrocortisone, hydrocortisone acetate, methyl salicylate, menthol, methyl nicotinate, capsaicin, capsaicin oleoresin and combinations thereof.

Another optional ingredient that may be present in the hydrogen peroxide foam of the instant invention are skin protectants. Skin protectants may be useful in treating topical wounds, as rough and/or bleeding skin may require comforting. These may include glycerin, propylene glycol, dimethicone, allantoin, aluminum hydroxide gel, calamine, cocoa butter, kaolin, petrolatum, shark liver oil, zinc acetate, zinc carbonate, zinc oxide, cod liver oil, lanolin, mineral oil, talc, topical starch, colloidal oatmeal, and sodium bicarbonate.

The foaming chamber that contains and dispenses the foam $H_2O_2$ may be an air-driven, that is, the foam-producing gas consists essentially of air. The foam produced by this device is an aerated foam. A preferred foam dispensing device comprises a reversibly compressible and decompressible container housing which operates at atmospheric pressure. A preferred foam dispensing device is one produced by Airspray N.V. which delivers creamy, high-quality foam without the use of non-air propellants. The type of foam dispensing device is similar to those currently in use in the liquid hand soap market. Typical of these is the Foam Blaster™ made by Johnson & Johnson and geared to the family consumer.

The foam dispensing system of this invention comprises a foam dispenser driven by air, oxygen or other oxygen-containing environmentally-acceptable and non-flammable gas. Representative air-driven foam dispensers suitable for self-administering foamed formulations in accordance with the method of this invention are devices designed for use in the upright or inverted position. All dispense foam in a propellantless manner in contrast to aerosol devices, which rely on a gaseous propellant initially pressurized within the device and maintained therein under pressure throughout its useful lifetime. The term "propellantless" as used herein refers to the preparation and delivery of foam in a way that avoids use of an initially pressurized gas to achieve rapid expansion of the gas (propellant) through an emulsion. The devices used in the self-administrable embodiment of this invention are propellantless in the sense that they rely on air to produce an aerated foam.

In one embodiment the air is initially incorporated into the device and maintained therein at substantially atmospheric pressure in a reversibly compressible and decompressible container. The air within the container can be brought to a state of increased pressure on demand, simply by compressing the container, e.g. by finger depressing it, thereby providing sufficient driving force to produce and dispense foam from the device. The devices are also designed to have their air supply automatically replenished by allowing the container to decompress, whereupon air is drawn from the outside atmosphere into the container through a valve which is open to the atmosphere during the decompression mode but closed during the compression mode.

The dispenser's compressible and decompressible container is conveniently composed of high density polyethylene or polypropylene.

A second embodiment of the uniquely compounded $H_2O_2$ of this invention is in the form of a spray mist. In this embodiment, an aqueous solution of $H_2O_2$ is dispensed by a consumer as a spray mist for the treatment of minor injuries comprising a 0.1% to 15% solution of $H_2O_2$ antiseptic which is combined with less than 1% of sodium pyrophosphate stabilizer and packaged in a container equipped with an aerosol or pump sprayer that ejects a fine mist of $H_2O_2$ topically to a wound. A preferred concentration of hydrogen peroxide in the spray embodiment is 3% by weight.

To make a laboratory quantity of 3% hydrogen peroxide spray mist, 8.68 grams of 35% $H_2O_2$ is placed in a beaker. 0.25 grams of sodium pyrophosphate is added and stirred until dissolved. Water is added to bring the total weight of the solution to 100 grams. The final solution is placed in a spray bottle which is pressed by a user to eject the peroxide mist as needed.

Optional ingredients that may be added to the hydrogen peroxide spray of this invention include topical pain relievers and skin protectants. The topical pain relievers may be benzocaine, butamben picrate, dibucaine hydrochloride, dimethisoquin hydrochloride, dyclonine hydrochloride, lidocaine, lidocaine hydrochloride, pramoxine hydrochloride, tetracaine, tetracaine hydrochloride, benzyl alcohol, camphor, camphorated metacresol, juniper, menthol, phenol, phenolate sodium, resorcinol, diphenhydramine hydrochloride, tripelenamine hydrochloride, hydrocortisone, hydrocortisone acetate, methyl salicylate, menthol, methyl nicotinate, capsaicin, capsaicin oleoresin and combinations thereof.

Another optional ingredient, skin protectants, may be glycerin, propylene glycol, dimethicone, allantoin, aluminum hydroxide gel, calamine, cocoa butter, kaolin, petrolatum, shark liver oil, zinc acetate, zinc carbonate, zinc oxide, cod liver oil, lanolin, mineral oil, talc, topical starch, colloidal oatmeal, and sodium bicarbonate.

The reasons for these optional ingredients in the $H_2O_2$ spray mist product are similar to the reasons stated above for their inclusion in the foam embodiment; to sooth and relieve pain associated with topical wounds. Another advantage of the foam and spray embodiments are their ability to be applied to a wound without the need for additional application means, such as cotton, which may be inconvenient and unsafe, since misapplication can lead to infection or additional injury.

A third embodiment of the uniquely compounded $H_2O_2$ of this invention is in the form of a disposable towelette. The towelette is a disposable towelette that is saturated with an aqueous solution of $H_2O_2$ (hydrogen peroxide) that packaged in a disposable wrapper. The solution comprises a 0.1% to 15% solution of $H_2O_2$ antiseptic and less than 1% of sodium pyrophosphate stabilizer. The packaging of this product enables the antiseptic application of $H_2O_2$ to a topical wound without additional applicator means. The consumer is insured of the safety and purity of the towelette if the packet containing it has not been opened. Additional application means in this embodiment are definitely not needed.

To make a laboratory quantity of 3% hydrogen peroxide solution that will be carried by disposable towelette, 8.68 grams of 35% $H_2O_2$ is placed in a beaker. 0.25 grams of sodium pyrophosphate is added and stirred until dissolved. Water is added to bring the total weight of the solution to 100 grams.

Optional ingredients that may be added to the hydrogen peroxide spray of this invention include topical pain relievers and skin protectants. The topical pain relievers may be benzocaine, butamben picrate, dibucaine hydrochloride, dimethisoquin hydrochloride, dyclonine hydrochloride, lidocaine, lidocaine hydrochloride, pramoxine hydrochloride, tetracaine, tetracaine hydrochloride, benzyl alcohol, camphor, camphorated metacresol, juniper, menthol, phenol, phenolate sodium, resorcinol, diphenhydramine hydrochloride, tripelenamine hydrochloride, hydrocortisone, hydrocortisone acetate, methyl salicylate, menthol, methyl nicotinate, capsaicin, capsaicin oleoresin and combinations thereof.

Another optional ingredient, skin protectants, may be selected from the group consisting of glycerin, propylene glycol, dimethicone, allantoin, aluminum hydroxide gel, calamine, cocoa butter, kaolin, petrolatum, shark liver oil, zinc acetate, zinc carbonate, zinc oxide, cod liver oil, lanolin, mineral oil, talc, topical starch, colloidal oatmeal, and sodium bicarbonate.

The reasons for these optional ingredients in the $H_2O_2$ towelette product are similar to the reasons stated above for the other forms of hydrogen peroxide embodied by this patent, namely the soothing of a topical injury as well as treatment with antiseptic.

A wide variety of materials can be used as the towelette substrate that is saturated with hydrogen peroxide. They should be of appropriate size, environmentally friendly for disposal, and be non-reactive with $H_2O_2$.

Examples of suitable substrates which meet the above criteria include non-woven substrates, woven substrates, hydroentangled substrates, air entangled substrates and the like. Preferred embodiments employ non-woven substrates since they are economical and readily available in a variety of materials. By non-woven is meant that the layer is comprised of fibers which are not woven into a fabric but rather are formed into a sheet, particularly a tissue. The fibers can either be random (i.e., randomly aligned) or they can be carded (i.e. combed to be oriented in primarily one direction). Furthermore, the non-woven substrate can be composed of a combination of layers of random and carded fibers.

Non-woven substrates may be comprised of a variety of materials both natural and synthetic. By natural is meant that the materials are derived from plants, animals, insects or byproducts. By synthetic is meant that the materials are obtained primarily from various man-made materials or from material that is usually a fibrous web comprising any of the common synthetic or natural textile-length fibers, or mixtures thereof.

Nonlimiting examples of natural materials useful in the present invention are silk fibers, keratin fibers and cellulosic fibers. Nonlimiting examples of cellulosic fibers include those selected from the group consisting of wood pulp fibers, cotton fibers, hemp fibers, jute fibers, flax fibers, and mixtures thereof. Wood pulp fibers are preferred while all cotton fibers (e.g. cotton pads) are normally avoided.

Substrates made from natural materials useful in the present invention can be obtained from a wide variety of commercial sources. Nonlimiting examples of suitable commercially available paper layers useful herein include Airtex.RTM., an embossed airlaid cellulosic layer having a base weight of about 71 gsy, available from James River Corporation, Green Bay, Wis.; and Walkisoft.RTM., an embossed airlaid cellulosic having a base weight of about 75 gsy, available from Walkisoft U.S.A., Mount Holly, N.C.

The disposable towelette is made of a material that is not reactive with $H_2O_2$. Typical materials used as disposable towelettes used for cleaning and for special purposes such contact lens maintenance are made of cellulosic tissue, rayon/polyester blends, silicone carbonates, polypropylene, polyethylene, and the like.

The substrate can be made into a wide variety of shapes and forms. In this invention, the substrate is a single use towelette. Advantageously, the towelettes are folded in a Z-shaped formation. This feature will aid in rapid opening and unfolding for quick use to wound treatment. The size of the towelette may range in length from 10 to 40 cm, preferably from 15 to 30 cm, optimally from 18 to 24 cm. The width of the towelette may range from 8 to 30 cm, preferably from 10 to 25 cm, optimally from 15 to 20 cm.

The fourth embodiment of this invention related to $H_2O_2$ in the form of a gel. An antiseptic gel composition of $H_2O_2$ (hydrogen peroxide) that comprises a) a 0.1% to 15% solution of $H_2O_2$ antiseptic;

b) about 2% hypromellose thickener;

c) about 0.25% sodium pyrophosphate stabilizer;

d) about 0.05% 2-amino-2-methyl-1-propanol neutralizing agent and the balance propylene glycol formulated into a stable gel composition that is dispensed by a consumer as needed for the treatment of minor injuries.

To make a laboratory quantity of hydrogen peroxide gel, 0.25 grams of sodium pyrophosphate is dissolved in a minimal amount of purified water. To the aqueous preservative is added about 2% hypromellose thickener, with stirring. Next is added 8.68 grams of 35% $H_2O_2$, and finally 0.05 grams of 2-amino-2-methyl-1-propanol or similar neutralizing agent is added. When these ingredients are blended, 96.75 grams of propylene glycol are added to the mixture. The $H_2O_2$ gel is now ready for packaging into suitable tubes or other squeezable containers.

Optional ingredients that may be present in the hydrogen peroxide gel embodiment of this invention include topical pain relievers and skin protectants. The topical pain relievers are used to kill pain which may accompany the wound being treated. They may be selected from the group consisting of benzocaine, butamben picrate, dibucaine hydrochloride, dimethisoquin hydrochloride, dyclonine hydrochloride, lidocaine, lidocaine hydrochloride, pramoxine hydrochloride, tetracaine, tetracaine hydrochloride, benzyl alcohol, camphor, camphorated metacresol, juniper, menthol, phenol, phenolate sodium, resorcinol, diphenhydramine hydrochloride, tripelenamine hydrochloride, hydrocortisone, hydrocortisone acetate, methyl salicylate, menthol, methyl nicotinate, capsaicin, capsaicin oleoresin and combinations thereof.

Another optional ingredient that may be present in the hydrogen peroxide foam of the instant invention are skin protectants. Skin protectants may be useful in treating topical wounds, as rough and/or bleeding skin may require comforting. These may include glycerin, propylene glycol, dimethicone, allantoin, aluminum hydroxide gel, calamine, cocoa butter, kaolin, petrolatum, shark liver oil, zinc acetate, zinc carbonate, zinc oxide, cod liver oil, lanolin, mineral oil, talc, topical starch, colloidal oatmeal, and sodium bicarbonate.

The use of hydrogen peroxide as a household antiseptic is very well known and widely used. Before applicants' invention, the use of $H_2O_2$ was limited in that a user needed application means, such as cotton, to use it. This made it inconvenient to use when traveling or in a variety of emergency situations. The bottle of hydrogen peroxide could easily become contaminated if foreign objects were introduced into it, or become ineffective if the bottle was left uncapped and the peroxide degrades into water and oxygen:

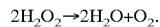

$$2H_2O_2 \rightarrow 2H_2O + O_2.$$

The foam, spray, gel, and towelette forms of $H_2O_2$ of this invention can be easily used without fear of contamination. The methods of use for each form can be applied to the wound site without dripping or running off the skin as has been the case in the past with $H_2O_2$ solutions sold as a home pharmacy staple. In each form of hydrogen peroxide claimed herein by applicants, the peroxide is able to come into contact with a wound without the need for additional application means and the peroxide can be applied to a wound site without dripping.

These product assets allow a user to apply the hydrogen peroxide towelettes, spray, foam, and gel when traveling or away from home or at other times when the user is without easy access to various application means. In the case of the towelette, the wound may be wiped repeatedly until it is spent; that is the $H_2O_2$ is used up and/or the towelette is dirty.

DISCUSSION

The stability and shelf life of the hydrogen peroxide formulations of the present inventions are noteworthy and quite surprising. The instability and short shelf-life of prior art liquid hydrogen peroxide have been difficult to overcome. Applicants have discovered ways to lengthen the shelf life of the instant embodiments and preserve the antiseptic properties of $H_2O_2$ by unique formulations that minimize exposure to air and light. A selection of optional ingredients available further improves the useful life of the embodiments presented herein. A good approximation of the shelf life of the foam, mist, towelette, and gel forms of this invention is approximately two years. The more time that the $H_2O_2$ embodiments are not exposed to air or light, the longer will be their useful life.

The embodiments each present the active ingredient at an optimal level to the skin of the wound. Each embodiment is able to hold the $H_2O_2$ on the wound site without the waste and run off that is common with the prior art, liquid product.

The stability and shelf-life of the foam $H_2O_2$ is especially remarkable as the $H_2O_2$ molecules remain intact after traveling through a vacuum chamber. This is despite the inherently unstable nature of the $H_2O_2$ molecule.

SCOPE OF THE INVENTION

The above presents a description of the best mode contemplated of carrying out the present invention, and of the manner and process of making and using it, in such full, clear, concise, and exact terms as to enable any person skilled in the art to which it pertains to make and use this invention. This invention is, however, susceptible to modifications and alternate constructions from that discussed above which are fully equivalent. Consequently, it is not the intention to limit this invention to the particular embodiments disclosed. On the contrary, the intention is to cover all modifications and alternate constructions coming within the spirit and scope of the invention as generally expressed by the following claims, which particularly point out and distinctly claim the subject matter of the invention.

What is claimed is:

1. An aqueous solution of $H_2O_2$ (hydrogen peroxide) that is dispensed for topical use as a stable foam for the treatment of minor skin injuries comprising
   a) a 0.1% to 15% solution of $H_2O_2$;
   b) about 1% of a surfactant;
   c) from about 0.05% to 1% of a stabilizer;
   d) at least one non-ingestable skin protectant; and
   e) at least one topical pain reliever
that is packaged in a container equipped with a pump foaming chamber that produces foam without the use of gas propellants and delivers $H_2O_2$ topically to a wound by finger-depression of a foam dispenser.

2. The peroxide foam of claim 1 wherein the surfactant is a non-ionic surfactant selected from the group consisting of octoxynol 9, laneth-4, steareth-4, oleth-4, ceteth-10, laneth-10, steareth-10, oleth-10, ceteth-20, polysorbates 20 and 80, and combinations thereof.

3. The peroxide foam of claim 1 wherein the stabilizer is sodium pyrophosphate.

4. The peroxide foam of claim 1 wherein the topical pain relievers are selected from the group consisting of benzocaine, butamben picrate, dibucaine hydrochloride, dimethisoquin hydrochloride, dyclonine hydrochloride, lidocaine, lidocaine hydrochloride, pramoxine hydrochloride, tetracaine, tetracaine hydrochloride, benzyl alcohol, camphor, camphorated metacresol, juniper, [menthol}, phenol, phenolate sodium, resorcinol, diphenhydramine hydrochloride, tripelenamine hydrochloride, hydrocortisone, hydrocortisone acetate, methyl salicylate, methyl nicotinate, capsaicin, capsaicin oleoresin and combinations thereof.

5. The peroxide foam of claim 1 wherein the non-ingestible topical skin protectants are selected from the group consisting of aluminum hydroxide gel, calamine, kaolin, petrolatum, dimethicone, talc, lanolin, and topical starch.

6. The foam of claim 1 wherein the $H_2O_2$ foam dispensing device comprises a reversibly compressible and decompressible container housing which operates at atmospheric pressure.

7. The peroxide foam of claim 1 wherein the shelf life is about two years.

8. A method for treating topical wounds of the skin with a composition of hydrogen peroxide ($H_2O_2$) which comprises applying a foam composition comprising from 0.1 to 15% hydrogen peroxide, stabilized with minor amounts of sodium pyrophosphate and formulated with a surfactant, at least one non-ingestible skin protectant, and at least one topical pain reliever to a wound site by depressing a finger-activated pump foaming device in the immediate vicinity of said wound allowing the peroxide to come into contact with the wound without the need for additional application means and allowing the peroxide to treat the wound without dripping off the skin surface to which it was applied.

9. The method of claim 8 wherein the topical pain reliever is selected from the group consisting of benzocaine, butamben picrate, dibucaine hydrochloride, dimethisoquin hydrochloride, dyclonine hydrochloride, lidocaine, lidocaine hydrochloride, pramoxine hydrochloride, tetracaine, tetracaine hydrochloride, benzyl alcohol, camphor, camphorated metacresol, juniper, phenol, phenolate sodium, resorcinol, diphenhydramine hydrochloride, tripelenamine hydrochloride, hydrocortisone, hydrocortisone acetate, methyl salicylate, methyl nicotinate, capsaicin, capsaicin oleoresin and combinations thereof.

10. The method of claim 8 wherein the non-ingestible topical sin protectants are selected from the group consisting of aluminum hydroxide gel, calamine, kaolin, petrolatum, dimethicone, talc, lanolin, and topical starch.

* * * * *

UNITED STATES PATENT AND TRADEMARK OFFICE
CERTIFICATE OF CORRECTION

PATENT NO. : 6,964,782 B1
DATED : November 15, 2005
INVENTOR(S) : Smith, RL et al.

It is certified that error appears in the above-identified patent and that said Letters Patent is hereby corrected as shown below:

Column 1,
Line 59, change "t the" to -- to the --.

Column 3,
Line 6, change "an easy" to -- and easy --.

Column 9,
Line 33, delete "[menthol}".

Column 10,
Line 38, change "sin" to -- skin --.

Signed and Sealed this

Twenty-first Day of February, 2006

JON W. DUDAS
*Director of the United States Patent and Trademark Office*